(12) United States Patent
Miyawaki et al.

(10) Patent No.: US 8,304,240 B2
(45) Date of Patent: Nov. 6, 2012

(54) MICROINJECTION METHOD AND DEVICE

(75) Inventors: Atsushi Miyawaki, Saitama (JP);
Hiroyuki Imabayashi, Tokyo (JP);
Sachiko Karaki, Tokyo (JP)

(73) Assignee: Olympus Corporation, Tokyo (JP)

(*) Notice: Subject to any disclaimer, the term of this patent is extended or adjusted under 35 U.S.C. 154(b) by 134 days.

(21) Appl. No.: 12/464,038

(22) Filed: May 11, 2009

(65) Prior Publication Data
US 2009/0286319 A1     Nov. 19, 2009

Related U.S. Application Data

(63) Continuation of application No. 10/552,923, filed as application No. PCT/JP2004/005167 on Nov. 11, 2005, now abandoned.

(30) Foreign Application Priority Data

Apr. 11, 2003 (JP) .................................. 2003-107267

(51) Int. Cl.
*C12N 15/00* (2006.01)

(52) U.S. Cl. ......................................... 435/455; 435/470

(58) Field of Classification Search ........................ None
See application file for complete search history.

(56) References Cited

U.S. PATENT DOCUMENTS

| | | | |
|---|---|---|---|
| 5,302,523 A | 4/1994 | Coffee et al. | |
| 5,464,765 A * | 11/1995 | Coffee et al. | 435/470 |
| 5,753,814 A * | 5/1998 | Han et al. | 73/105 |
| 6,063,629 A | 5/2000 | Knoblauch | |
| 6,770,480 B1 * | 8/2004 | Canham | 435/458 |
| 2003/0228695 A1 * | 12/2003 | Nakamura et al. | 435/455 |

FOREIGN PATENT DOCUMENTS

| | | |
|---|---|---|
| JP | 1-112976 | 5/1989 |
| JP | 3-119989 | 5/1991 |
| JP | 5-192171 | 8/1993 |
| JP | 05-300946 | 11/1993 |
| JP | 6-343478 | 12/1994 |
| JP | 10-179174 | 7/1998 |
| JP | 2003-88383 | 3/2003 |
| JP | 2003-325161 | 11/2003 |
| WO | WO 99/46361 | 9/1999 |

OTHER PUBLICATIONS

Japanese Official Action dated Mar. 2, 2010.
Yamamoto, F., et al., "The Pricking Method", Experimental Cell Research, 1982, pp. 79-84, vol. 142.

* cited by examiner

*Primary Examiner* — Jim Ketter
(74) *Attorney, Agent, or Firm* — Scully, Scott, Murphy & Presser, PC

(57) ABSTRACT

An object of the present invention is to provide a method for introducing a physiologically active substance such as a gene into a cell, which introduces a physiologically active substance such as any given gene into any given cell in a view under a microscope, while significantly reducing invasiveness to the cell, and a device used for the above method. The present invention provides a method for introducing a physiologically active substance into a cell, which comprises: allowing a physiologically active substance to attach around a needle having a diameter of 500 nm or less, provided that it is able to be inserted into a cell; and inserting the above-described needle into the cell; and a microinjection device for carrying out the aforementioned method.

1 Claim, 8 Drawing Sheets

MICROINJECTION METHOD AND DEVICE

CROSS-REFERENCE TO RELATED APPLICATION

This application is a continuation application of U.S. patent application Ser. No. 10/552,923 filed Aug. 4, 2006, which claims benefit of Japanese Patent Application No. 107267/2003 filed Apr. 11, 2003, the entire contents of each of which are incorporated herein by reference.

TECHNICAL FIELD

The present invention relates to a method for introducing a physiologically active substance into cells and a microinjection device used for the above method.

BACKGROUND ART

Examples of a technique of introducing gene DNA into cultured cells or the like may include the calcium precipitation method, the lipid transfer method, the viral vector method, electroporation, the gene gun method, and the microinjection method. In the above methods other than the microinjection method, DNA is introduced in cells at a certain probability, and thus it is impossible to introduce DNA into only a specific cell. On the other hand, the microinjection method has been problematic in that since the diameter of the edge of a glass pipette is approximately 1 μm, cells are easily damaged when such a glass pipette is inserted into the cell nucleus thereof. In addition, when different genes are introduced into multiple cells, the same number of pipettes as that of genes should be prepared, resulting in complicated preparation.

Japanese Patent Application Laid-Open No. 2003-88383 discloses that in order to provide a means for collecting biomolecules such as RNA from living cells, a needle capable of specifically binding to biomolecules is inserted into a living cell using a device enabling fine position control, and that the needle is then removed from the cell. As a needle used herein, a ZnO whisker or a carbon nanotube is used. For example, the surface of a metal oxide whisker is modified with an amino group, so that the whisker can bind to biomolecules existing in cells and collect them.

DISCLOSURE OF THE INVENTION

As mentioned above, the conventional electroporation or gene gun is able to inject a substance into large quantities of cells at a time. However, it has been difficult to inject a substance into a specific cell. Moreover, the conventional microinjection is able to inject a substance into a specific cell. However, since a hollow glass capillary has been used as a needle to be injected, there has been a certain limit regarding reduction in the external diameter thereof. Thus, these conventional methods have been problematic in that a cell bursts or suffers fatal damage when a needle is injected therein, or in that operations become complicated.

As described in Japanese Patent Application Laid-Open No. 2003-88383, it is possible to collect biomolecules from living cells by performing specific modification on a metal oxide whisker or a carbon nanotube. It is also possible to successively record a change in each of the cells over time. However, a method for successively recording the change in such a cell over time by actively introducing a gene therein has not yet been disclosed. In addition, the aforementioned method has been problematic in that the method comprises a complicated step of modifying the surface of a needle with a substance that is allowed to specifically bind to biomolecules.

It is an object of the present invention to solve the aforementioned problems of the prior art techniques. In other words, it is an object of the present invention to provide a method for introducing a physiologically active substance such as a gene into a cell, which introduces a physiologically active substance such as any given gene into any given cell in a view under a microscope, while significantly reducing invasiveness to the cell, and a device used for the above method.

As a result of intensive studies directed towards achieving the aforementioned object, the present inventors have found that the object can be achieved by using a needle having a diameter of 500 nm or less, provided that it is able to be inserted into a cell, and by inserting the above-described needle into the cell, thereby completing the present invention.

Thus, the present invention provides a method for introducing a physiologically active substance into a cell, which comprises: allowing a physiologically active substance to attach around a needle having a diameter of 500 nm or less, provided that it is able to be inserted into a cell; and inserting the above-described needle into the cell.

Preferably, a needle having a diameter between 50 and 100 nm, provided that it is able to be inserted into a cell, is used.

Preferably, a needle having a length of 5 μm or less is used.

Preferably, a needle having a taper form, provided that it is able to be inserted into a cell, is used.

Preferably, a needle composed of a carbon nanotube is used.

Preferably, a needle composed of silicon is used.

Preferably, a needle composed of a metal oxide is used.

Preferably, a needle having a diameter between 50 and 500 nm, provided that it is able to be inserted into a cell, has electrical conductivity.

Preferably, the physiologically active substance is DNA, RNA, or a protein.

Preferably, using a needle charged with an electrical charge opposite to that of a physiologically active substance, the physiologically active substance is allowed to electrostatically attach to the above-described needle, and the above-described needle is then inserted into a cell.

Preferably, using a needle to which a voltage opposite to the charge of a physiologically active substance has been applied, the physiologically active substance is allowed to electrically attach to the above-described needle, and the above-described needle is then inserted into a cell.

Preferably, after a negatively charged physiologically active substance has been allowed to electrostatically attach to a needle that is positively charged, the above-described needle is inserted into a cell, and the needle is then negatively charged, so that the physiologically active substance is allowed to detach from the needle.

Preferably, after a negatively charged physiologically active substance has been allowed to electrostatically attach to a needle to which a positive voltage has been applied, the above-described needle is inserted into a cell, and a negative voltage is then applied to the needle, so that the physiologically active substance is allowed to detach from the needle.

Preferably, negative voltages that change over time are applied to the needle, so that the physiologically active substance is allowed to detach from the needle.

Preferably, the voltages that change over time are multiple pulse voltages.

Preferably, the needle to which a voltage opposite to the charge of a physiologically active substance is applied, is controlled in terms of voltage value and the time required for application of the voltage.

Preferably, the method of the present invention comprises the following steps:
(1) a step of positively charging a needle;
(2) a step of immersing the needle in a solution comprising a negatively charged physiologically active substance, so that the physiologically active substance is allowed to attach around the needle;
(3) a step of inserting the needle into a target site in a cell, and then applying a negative voltage to the needle, so that the physiologically active substance is allowed to detach from the needle;
(4) a step of removing the needle from the cell; and
(5) a step of repeating the above-described steps (1) to (4), so as to introduce at least one desired, identical or different, physiologically active substance into each of multiple cells.

In another aspect, the present invention provides a microinjection device, which comprises: a needle having a diameter between 50 and 500 nm, provided that it is able to be inserted into a cell; a driving means for controlling the movement of the above-described needle that enables insertion of the above-described needle into the cell and the removal therefrom; and a voltage-applying means for applying a voltage to maintain a physiologically active substance on the surface of the above-described needle or to remove it from the above surface, wherein the above-described needle is inserted into a cell and that the physiologically active substance is then introduced into the cell.

In another aspect, the present invention provides a microinjection device used for the aforementioned method of the present invention, which comprises: a needle having a diameter between 50 and 500 nm, provided that it is able to be inserted into a cell; a driving means for controlling the movement of the above-described needle that enables insertion of the above-described needle into the cell and the removal therefrom; and a voltage-applying means for applying a voltage to maintain a physiologically active substance on the surface of the above-described needle or to remove it from the above surface, wherein the above-described needle is inserted into a cell and that the physiologically active substance is then introduced into the cell.

Preferably, a microinjection device, which comprises a cell-retaining means for retaining a cell at a certain site and a microscope for observing the cell that is retained in the cell-retaining means, is provided.

Preferably, a microinjection device, which comprises a vessel for receiving the physiologically active substance, is provided.

Preferably, the microscope for observing the cell is provided with a means for maintaining culture environment.

Preferably, the driving means for controlling the movement of the above-described needle, which is connected to the needle, is a piezoelectric element.

Preferably, by the driving means for controlling the movement of the above-described needle, the needle is inserted into a cell from the direction of gravitational force.

Preferably, by the driving means for controlling the movement of the above-described needle, the needle is descended to a certain height with respect to the surface of the cell-retaining means.

Preferably, a microinjection device which comprises a washing tank for eliminating the physiologically active substance attached to the surface of the above-described needle, is provided.

Preferably, the above-described washing tank is used to perform at least one selected from sterilized water washing, alkali washing, and acid washing.

Preferably, the time required for application of a voltage to the above-described needle is shorter than the time at which the above-described needle stays in a cell.

Preferably, the above-described cell is contained in a culture solution, in which physiologically active substances are dispersed.

In another aspect, the present invention provides a microinjection device, which comprises: a culture solution, in which physiologically active substances are dispersed; a cell-retaining means for retaining a cell at a certain site; a needle having a diameter between 50 and 500 nm, provided that it is able to be inserted into the cell; a driving means for controlling the movement of the above-described needle, which is connected to the needle; and a microscope for observing the cell retained in the cell-retaining means; wherein the above-described needle forms a hole that constitutes a pathway for introducing the physiologically active substance into the cell.

In another aspect, the present invention provides a method for introducing a physiologically active substance into a cell, which comprises performing microinjection using the aforementioned microinjection device of the present invention.

Figure 1:
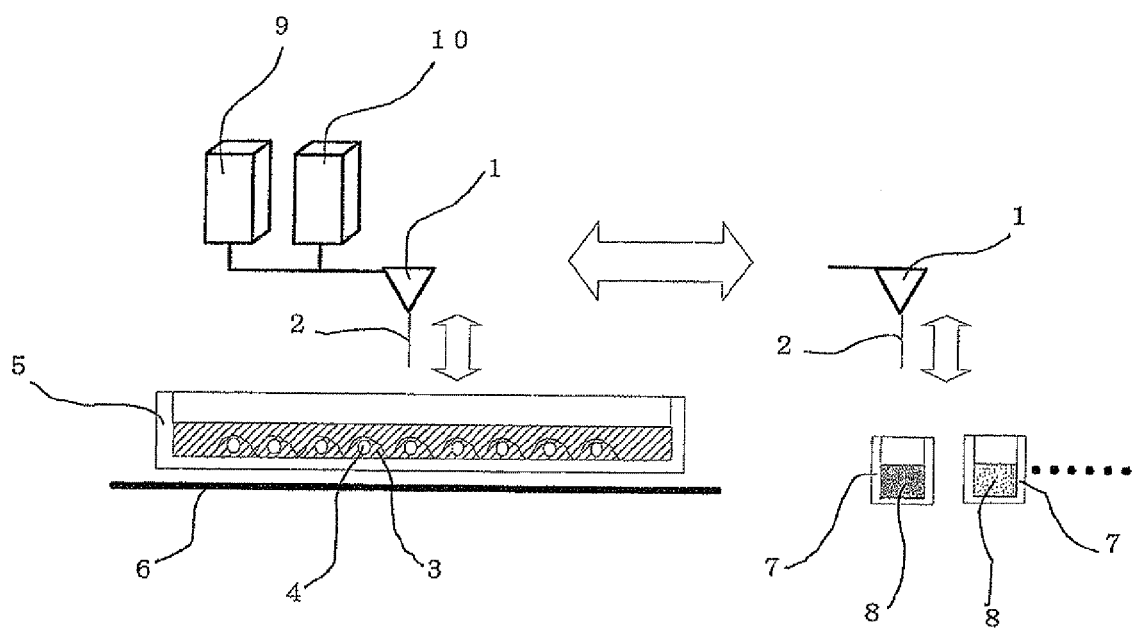
FIG. 1 shows a summary of the method of the present invention.

In the above drawings, 1 represents a cantilever, 2 represents a needle, 3 represents a cell, 4 represents a cell nucleus, 5 represents a petri dish, 6 represents a cell-retaining means, 7 represents a vessel, 8 represents a solution containing a physiologically active substance, 9 represents a driving means, 10 represents an electric potential-controlling means, 11 represents a microinjection device, 12 represents an incubator, 13 represents a heater, 14 represents a fan, 15 represents an object glass, 16 represents a specimen, 17 represents a light source used for transillumination, 18 represents a vessel, 19 represents a washing tank, 20 represents an XY stage, 21 represents a needle, 22 represents a stacked piezoelectric actuator, 23 represents a fixed block, 24 represents a Z-axis stage, 25 represents the bottom of a petri dish, 26 represents a cell, 27 represents a cell nucleus, 28 represents gene DNA, and 29 represents a pinhole.

BEST MODE FOR CARRYING OUT THE INVENTION

The embodiments of the present invention will be described in detail below.

In the method of the present invention, a physiologically active substance is allowed to attach around a needle having a diameter of 500 nm or less, and the above needle is then inserted into a cell, so as to introduce the physiologically active substance into the cell.

The present invention is characterized in that an extremely thin needle (to such an extent that it exceeds optical resolution) is used for gene introduction. Specifically, a needle having a diameter of 500 nm or less, and particularly preferably having a diameter between 50 and 100 nm, can be used, provided that it is able to be inserted into a cell. The needle used in the present invention is preferably a needle, the electrical properties of which, such as electrification, can easily be controlled. In the present invention, for example, the surface of the needle is positively charged, and DNA molecules are allowed to attach to the surface. Thereafter, the needle is inserted into the cell nucleus, and the surface of the needle is then negatively charged, so as to allow the DNA molecules to detach from the surface of the needle. Since a thin needle is used in the present invention, damage given to the cell can be reduced to a minimum, and further, any given DNA can be introduced into any given target cell.

It has been known that when cell organelle (Golgi body, mitochondrion, and the like) is damaged with a needle, the survival rate of the cell decreases. When a needle having a diameter between 50 and 500 nm is used, provided that it is able to be inserted into a cell, such a needle is small enough with respect to the size of a cell nucleus, and thus it hardly hurts cell organelle other than the cell nucleus. Moreover, by allowing the needle to proceed to the cell from the position directly above (from the direction of gravitational force), the needle can be inserted into a site at which the cell nucleus is closest to the cell membrane. Herein, the probability that the cell organelle exists in a very small space between the cell nucleus and the cell membrane is low. From this viewpoint as well, the cell organelle is hardly damaged, and thus the survival rate of cell can be improved.

In the present invention, only the use of a needle having a surface with conductivity (electrification) is required. Modification of the surface of the needle depending on biomolecules is not particularly necessary.

For example, 100 types of DNA solutions and 100 cells are prepared. Thereafter, a needle is immersed in such a DNA solution, and the needle is then inserted into such a cell from the position directly above the cell. Such an operation to immerse a needle in a DNA solution and an operation to insert the needle into the cell are repeated, so that desired individual DNAs can be introduced into different cells, and so that the cells can individually be transformed. Therefore, according to the method of the present invention, screening of an agent or exhaustive analysis of interaction between biomolecules can be carried out at a single cell level, differing from the conventional methods wherein such screening or analysis is carried out at a well level, using a 96-well plate or 384-well plate.

The material of the needle used in the present invention is not particularly limited, as long as it has the aforementioned properties. For example, a carbon nanotube can be used as a needle. Such a carbon nanotube has a cylindrical form obtained by winding a monolayer graphite (graphin), and it is a microcrystal composed of 100% carbon atoms. In recent years, nanotechnology has become a focus of attention, and such a carbon nanotube has also received attention in various fields. Examples of studies regarding the use of a carbon nanotube include the development of a screen in which a nanotube is used for electron gun, in place of liquid crystal or plasma display; application of a carbon nanotube to fuel cells and solar cells; and the use as a material for hydrogen storage. A carbon nanotube can be applied to the aforementioned techniques because it has various types of characteristic properties such as minuteness, the properties as a quantum obtained from its three-dimensional structure, and its composition purely consisting of carbons, and thus because it has unique properties different from those of the conventional materials. In addition, a carbon nanotube purely consists of carbons. Thus, differing from carbon black and the like, it contains almost no impurities. Moreover, a carbon nanotube is also characterized in that it does not change even after it has been exposed to a high temperature during a molding process and/or when it is used.

At present, as a multi wall carbon nanotube, a carbon nanotube having a diameter between approximately 50 and 100 nm and a length of 3 μm or more is available. It is preferable to use such a carbon nanotube in the present invention. If the diameter of a needle is too thin, the amount of a physiologically active substance that can be retained by the needle decreases. In contrast, if the diameter is too thick, the invasiveness to a cell increases. Thus, both cases are unfavorable. Accordingly, in the present invention, a needle having a diameter of 500 nm or less, and more preferably a diameter between 50 and 100 nm, is used, provided that it is able to be inserted into a cell. With regard to the length of a needle, since the height of a common cultured cell is approximately 5 μm, a needle having a length of 5 μm or less can appropriately be used. For example, a needle having a length of approximately 3 μm can be used.

Except for the aforementioned examples, the following needles can also be used.

A needle, which is produced by coating a metal oxide whisker shown in the aforementioned example of prior art technique with gold (Au) or platinum (Pt) using evaporation or sputtering device or the like, so as to impart electric conductivity to the surface thereof, can be used. Moreover, a needle, which is produced by coating a cantilever made from silicon that has frequently been used as a cantilever for an atomic force microscope with gold (Au) or platinum (Pt) using evaporation or sputtering device or the like, so as to impart electric conductivity to the surface thereof, can also be used. The needlepoint of such a cantilever made from silicon is etched using a device such as IPC or FIB for acumination, and a conductive membrane is then formed thereon, thereby further reducing the invasiveness to living cells. Furthermore, in the case of a cantilever made from silicon, the needlepoint thereof is converted to a taper form by etching, thereby improving the strength of the needle. In order to reduce damage given to a cell, it is necessary for the aforementioned needle to have a diameter between 50 and 500 nm, provided that it is able to be inserted into the cell. In the case of the aforementioned needle having a taper form also, the needle has a diameter between 50 and 500 nm, provided that it is able to be inserted into the cell.

The type of a physiologically active substance that can be introduced into a cell by the method of the present invention is not particularly limited. Examples thereof may include nucleic acids such as DNA or RNA and proteins. A preferred example may be a nucleic acid. As such a nucleic acid, either DNA or RNA may be used. In addition, examples of DNA used herein may include genomic DNA or a fragment thereof, cDNA, and synthetic DNA such as a synthetic oligonucleotide.

In the present invention, a needle having a diameter between 50 and 500 nm provided that it is able to be inserted into a cell as mentioned above (that is, a carbon nanoprobe or a metal oxide whisker having a conductive surface), is attached to the tip of the cantilever of an atomic force microscope (AFM), thereby producing electrical connection. The term "electrical connection" is herein used to mean electrical connection for positively or negatively controlling the charge of the needle. This cantilever works with the image processing of the microscope and moves between a vessel containing a physiologically active substance of interest and a cell of interest (a cell nucleus or the like), so that the physiologically active substance of interest can be introduced into only the cell of interest. In a preferred embodiment of the present invention, the needle is always positioned in the vertical direction, and it controls its needlepoint position at high accuracy.

The aforementioned movement of the needle can be conducted by a driving means for controlling the movement of the needle. That is to say, the present invention provides a microinjection device comprising: a needle having a diameter between 50 and 500 nm, provided that it is able to be inserted into a cell; and a driving means for controlling the movement of the above needle. More specifically, the microinjection device of the present invention comprises: (a) a cell-retaining means for retaining a cell at a certain site; (b) a needle having a diameter between 50 and 500 nm, provided that it is able to be inserted into the cell, and a driving means for controlling the movement of the above needle, which is connected to the above needle; and (c) a microscope for observing the cell retained in the cell-retaining means.

In the present invention, using a needle charged with an electrical charge opposite to that of a physiologically active substance, the physiologically active substance may be allowed to electrostatically (electrically) attach to the above needle, and the needle may be then inserted into a cell. When a physiologically active substance having a negative electric charge, such as DNA, is introduced into a cell, the above physiologically active substance is allowed to electrostatically (electrically) attach to a needle that is positively charged, and the needle may be then inserted into the cell.

In the present invention, utilizing the electrical polarity of a physiologically active substance, such a physiologically active substance may be allowed to attach to the surface of a needle for a certain period of time, or may be allowed to detach therefrom. That is, needless to say, such a physiologically active substance may be not only allowed to electrostatically attach to the surface of a needle, but it may be also allowed to attach thereon even in a state where a voltage is continuously applied to the needle. Thus, it is also possible that the physiologically active substance may be allowed to detach from the surface of the needle by reversing (inversing) the polarity of the voltage applied.

As mentioned above, a method for applying a voltage to a needle is not necessarily limited to electrostatic action, but it can be selected depending on the electrical properties of the physiologically active substance or the purpose of use. Thus, the present invention can be applied to various purposes.

As an example, the method of the present invention comprises the following steps:
(1) a step of positively charging a needle;
(2) a step of immersing the needle in a solution containing a negatively charged physiologically active substance, so that the physiologically active substance is allowed to attach around the needle;
(3) a step of inserting the needle into a target site in a cell, so as to introduce the physiologically active substance into the cell;
(4) a step of removing the needle from the cell, and then negatively charging the needle, so as to eliminate the physiologically active substance remaining around the needle; and
(5) a step of repeating the above-described steps (1) to (4), so as to introduce at least one desired, identical or different, physiologically active substance into each of multiple cells.

Hereafter, an example of the embodiments of the present invention will be described with reference to drawings.

FIG. 1 shows a summary of the method of the present invention. FIG. 1 shows with a double-headed arrow that a needle 2 equipped in a cantilever 1 that is connected to a driving means 9 moves between the position directly above a cell 3 and the position directly above a vessel 7 comprising a solution 8 containing a physiologically active substance. The cell 3 is cultured in a petri dish 5, and the petri dish 5 is placed on a cell-retaining means 6.

First, the needle 2 is inserted into the vessel 7 comprising the solution 8 containing a physiologically active substance, so that the solution containing the physiologically active substance is allowed to attach to the surface of the needle 2. Such attachment of the above solution takes place as a result of the control of the charge of the needle by an electric potential-controlling means, which is electrically connected to the needle 2. Namely, when the physiologically active substance is a negatively charged substance such as a nucleic acid, the physiologically active substance is allowed to efficiently attach to the needle 2 by positively charging the needle 2 by the electric potential-controlling means 10 in advance.

Subsequently, the needle 2, to which the physiologically active substance has been attached, is lifted up, so that it is removed from the vessel 7 comprising the solution 8 containing the physiologically active substance. Thereafter, the needle moves in the horizontal direction, and it is then disposed at the position directly above the cell of interest 3. The needle 2 disposed at the position directly above the cell 3 moves downwards, so that it can be inserted into a cell nucleus 4 in the cell of interest 3. The needle inserted into the cell nucleus 4 then releases the physiologically active substance attached to the surface thereof to the inside of the cell nucleus 4 under the status quo. The physiologically active substance can be released by controlling the charge of the needle by the electric potential-controlling means 10, which is electrically connected to the needle 2. Namely, when the physiologically active substance is a negatively charged substance such as a nucleic acid, the needle 2 is negatively charged by the electric potential-controlling means 10, so that the physiologically active substance can efficiently be released from the needle 2. After the physiologically active substance has been released to the inside of the cell nucleus 4, the needle is removed from the cell. Thereafter, the aforementioned operations are repeated, so as to introduce the desired physiologically active substance into the desired cell nucleus. The aforementioned movements of the needle 2 are all controlled by the driving means 9.

The present invention further relates to a microinjection device, which comprises: a needle having a diameter between 50 and 500 nm, provided that it is able to be inserted into a cell; a driving means for controlling the movement of the above needle that enables insertion the above needle into the cell and the removal therefrom; and a voltage-applying means for applying a voltage so as to retain a physiologically active substance on the surface of the above needle or to remove it from the surface thereof, wherein the above needle is inserted into the cell, so as to introduce the physiologically active substance into the cell.

The above microinjection device will be described in detail below.

Figure 2:
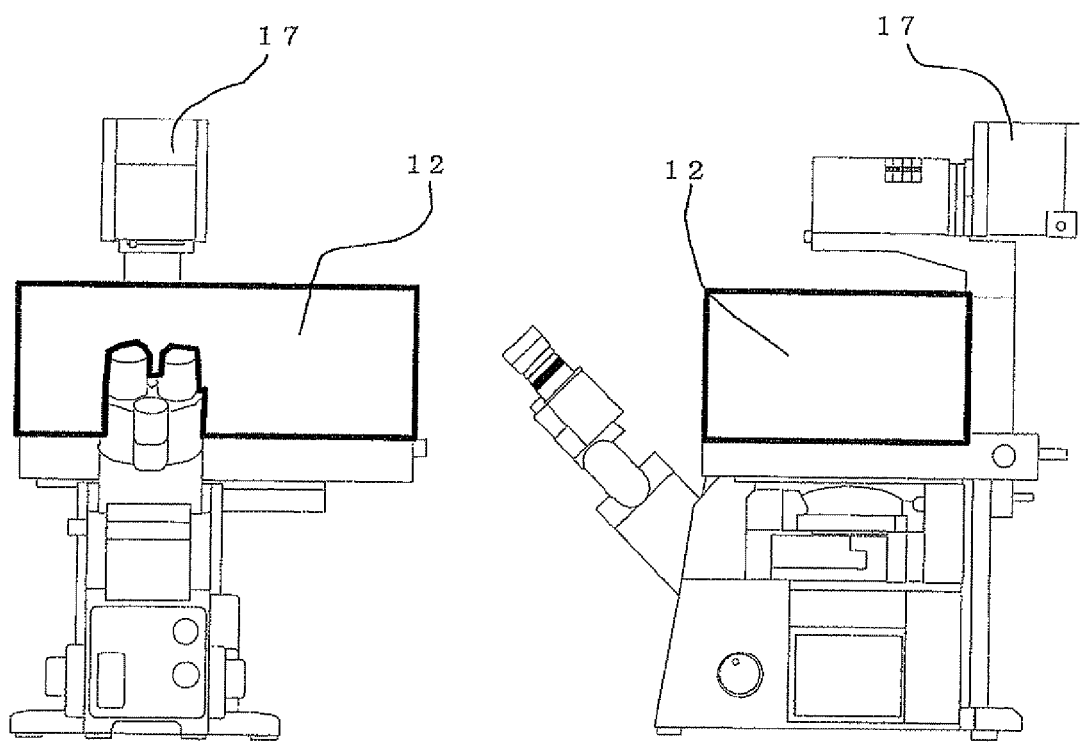
FIG. 2 shows a microinjection device constructed on the stage of an inverted microscope.

As shown in FIG. 2, the microinjection device is constructed on the stage of an inverted microscope, enabling the observation and/or measurement of the process from initiation of gene introduction to the subsequent course. On the microscope stage, an incubator 12 for maintaining the temperature at 37° C. is constructed, and the microinjection device is installed in the incubator.

Figure 3:
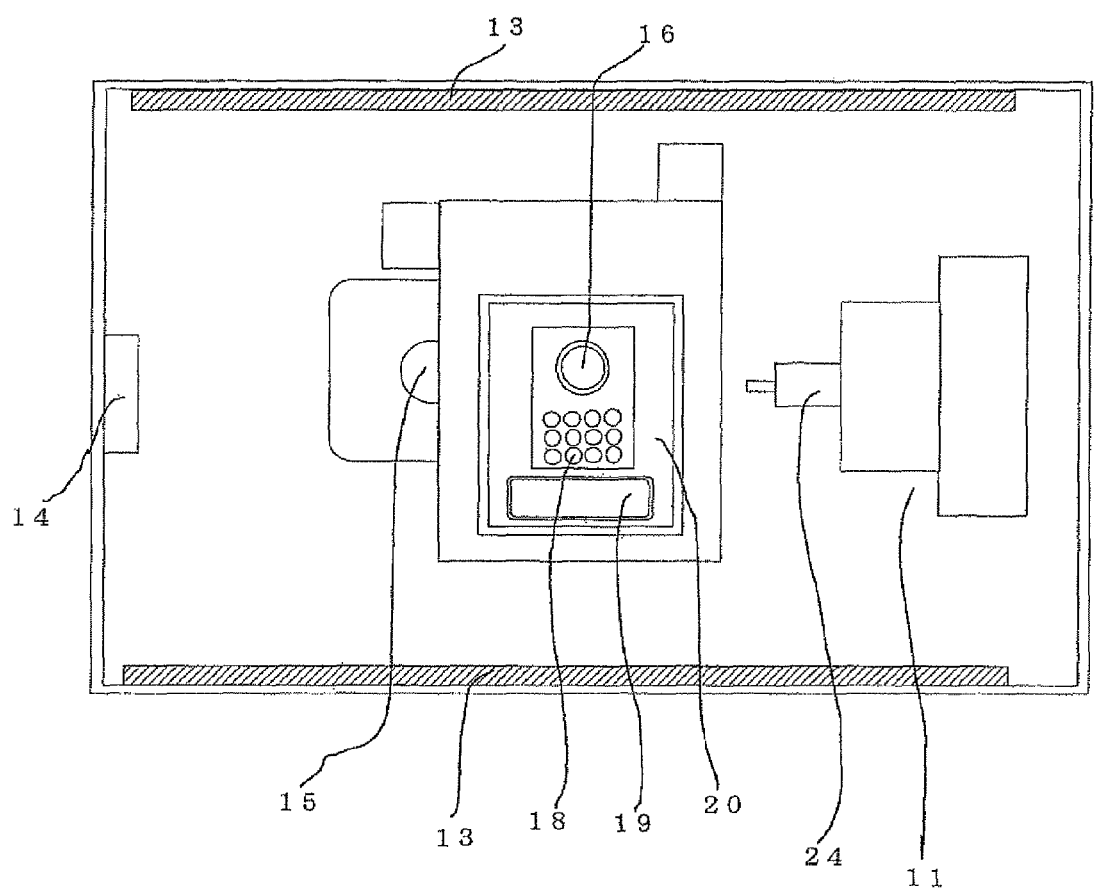
FIG. 3 is a top view of the microscope stage (the internal view of an incubator).

FIG. 3 is a top view of the microscope stage (the internal view of an incubator). The incubator is composed of a metal having excellent heat conductivity (an aluminum alloy or the like). A heater 13 or a fan 14 for stirring the internal air is disposed on the internal side of the incubator. The external surface of the incubator is covered with a heat insulator in order not to release the heat to the external environment. In addition, in order to observe the inside of the incubator with an inverted microscope, some regions on the top and bottom surfaces of the incubator are made from glass, so that a specimen 16 (a cell in a petri dish or the like) can be observed with an object glass 15. Moreover, a light from a light source for transillumination can be applied to the specimen, so that phase difference observation or differential interference observation can be conducted.

In order to optimize the pH of a cell culture solution to the culture environment, 5% $CO_2$ is supplied from the outside of the incubator through a tube, and using a fan, the inside of the incubator is uniformly filled with 5% $CO_2$.

On the microscope stage formed in the incubator, a petri dish acting as a specimen (a dish, a microplate, or the like), a vessel 18 comprising a solution containing gene DNA, such as a sample cup, a washing tank 19 for washing the needle, and the like, are placed on an XY stage 20 that is operated with a motor or the like.

Accordingly, the specimen 16, the vessel 18, and the washing tank 19 are able to move under a needle used for gene introduction. Thus, as stated above, the whole area in the specimen can be observed.

Figure 4:
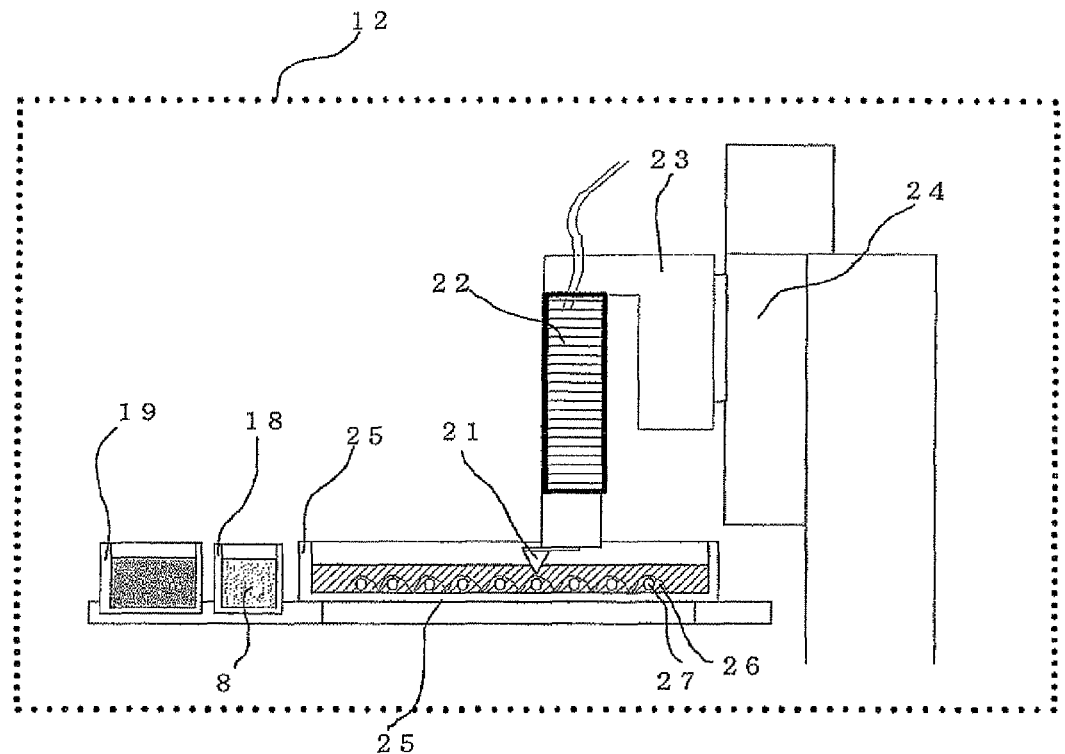
FIG. 4 shows the positions of the microinjection device and of the needle used for gene introduction.

A needle 21 used for gene introduction moves only in the Z direction (in the direction of gravitational force), and thus, it moves up and down with respect to the target that is positioned under the needle. As shown in FIG. 4, the needle 21 used for gene introduction is disposed, with the needlepoint thereof directed downwards, with respect to one end face of a stacked piezoelectric actuator 22 formed by lamination of thin piezoelectric elements (lead zirconate titanate). The other end face of the stacked piezoelectric actuator 22 is disposed on a fixed block 23. When a voltage is applied to the stacked piezoelectric actuator 22, the needle 21 slightly moves down. A voltage of approximately 100 V realizes a movement of 10 μm, although it depends on the type of a commercially available stacked piezoelectric actuator. Such amount of displacement can be controlled with the value of the voltage applied.

Further, the fixed block 23 is mounted on a Z-axis stage 24. With regard to the position of the needle 21 in the Z direction, by a two-step driving mechanism in which rough movements are controlled with the Z-axis stage 24 and fine movements are controlled with the stacked piezoelectric actuator 22, the needle 21 is inserted into the cell 26. For example, the needle 21 is positioned above a petri dish acting as the specimen 16, it roughly moves to the vicinity of the cell 26 in the petri dish, and thereafter, when the needle 21 is inserted into the cell 26, it finely moves. Since the needle 21 is very easily broken, the movement is terminated immediately before the needlepoint is allowed to come into contact with the bottom of the specimen 16 such as a petri dish (for example, at a height of 1 μm from the bottom).

That is to say, the needle 21 may pass through a cell nucleus 27. This microinjection device can easily be automated by allowing the device to recognize only the step of constantly lifting down the needlepoint to a height of 1 μm from the bottom. In particular, the control action to detect the surface of a cell membrane and lift down the needlepoint several μm from the position of the above surface is unnecessary, and thus expensive detection components can be reduced.

On the other hand, when the needle is lifted down to the vessel 18 filled with a gene DNA solution or to the washing tank 19, strict height control is unnecessary, and thus only the rough movement is applied by the Z-axis stage 24.

The movement of the microinjection device is as described above. It comprises the following steps.

(1) Washing of the Needle

Figure 5:
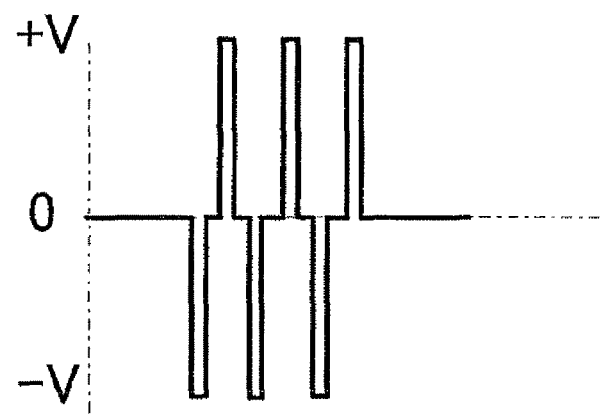
FIG. 5 shows the alternate voltage±5 V at 100 Hz that is used as a voltage to be applied.

The washing tank 19 is positioned under the needle 21 for gene introduction, and thus the needle 21 is lifted down into the washing tank 19. Washing solution (sterilized water) or the like is stored in the washing tank 19. An alternate voltage is applied to the needle 21 in a state where the needle is completely immersed in the washing solution. Thus, dusts or gene DNA that has previously been allowed to attach to the needlepoint are eliminated thereby. For example, as shown in FIG. 5, the alternate voltage±5 V at 100 Hz is applied as a voltage to be applied. Thereby, impurities remaining on the surface of the needle are eliminated. Preferably, the washing tank 19 may be subjected to ultrasonic washing, or two tanks may be established to wash with agents such as acid or alkali and also to wash with sterilized water.

(2) Thereafter, the needle 21 is lifted up from the washing tank 19. During such a step, the needlepoint may be dried by air blowing or the like.

(3) Subsequently, the vessel 18 containing a gene DNA solution moves under the needle 21, and the needle is then lifted down therein. A positive voltage is applied to the surface of the needle in a state where the needle is immersed in the solution. For example, a voltage to be applied is set at 1 V, and the time required for application of such a voltage is set to be 3 seconds or more. Since the gene DNA has a negative polarity, it is allowed to attach to the surface of the needle. Thereafter, the needlepoint is lifted up, and the specimen 16 is disposed under the needle. During this step, a voltage may be applied to or may not be applied to the needlepoint.

(4) When the needlepoint is lifted down into a petri dish of the specimen 16, application of the voltage to the needle 21 is terminated. The needlepoint is lifted down to the vicinity of the cell surface by rough movement, and thereafter, the needle 21 is inserted into the cell nucleus 27 by fine movement.

Figure 6:
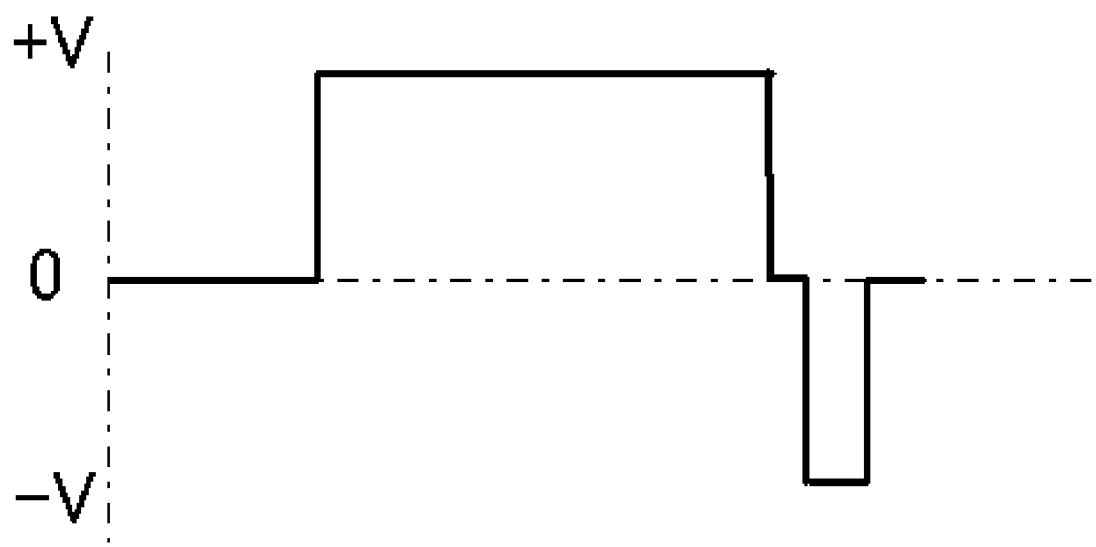
FIG. 6 shows a voltage waveform obtained during the period ranging from the retention of gene DNA to the release thereof.

(5) After the movement of the needle 21 has been terminated, a negative voltage is applied to the needlepoint, so that the gene DNA on the surface of the needle is allowed to detach therefrom, thereby being released into the cell (into the cell nucleus). For example, a voltage to be applied is set to be −0.5 V, and the time required for application of such a voltage is set to be approximately 1 second. (It is desired to apply a voltage for a time sufficient for the gene DNA attached to the needle to be detached therefrom.) FIG. 6 shows a voltage waveform obtained during the period ranging from the retention of the gene DNA to the release thereof.

(6) After completion of the application of the voltage, the needle 21 is lifted upwards, and the needle 21 is then washed in the washing tank 19. Thereafter, different gene DNA is allowed to attach to the surface of the needle in a vessel containing the different gene DNA, and it is then released into another cell.

Thus, when gene DNA attached to the surface of the needle 21 is released into a cell, a negative voltage is applied to the needle, only when the needle 21 stays in the cell, so that the gene DNA can be detached from the needle by electric repulsion. When a voltage is applied to the needle in a culture solution, there are concerns about formation of bubbles as a result of an electrochemical reaction. Thus, in a culture solution, it is desired to apply a voltage only for a necessary time. Accordingly, it is adequate that a voltage be applied only when the needle stays in the cell, and that such application of the voltage be terminated during a travel time necessary for the needle to be inserted into the cell and another travel time necessary for the needle to be removed from the cell.

Figure 7:
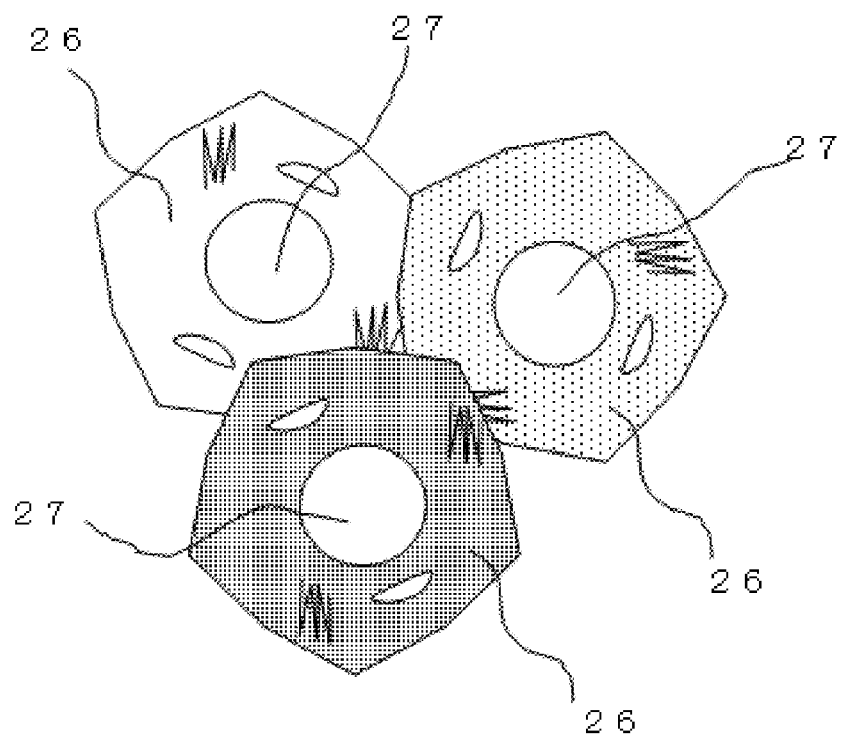
FIG. 7 shows the state of cells that are adjacent to each other.

By repeating these operations, it becomes possible to introduce each different gene DNA into cells 26 adjacent to each other, as shown in FIG. 7, and this technique can be used for the analysis of interaction between cells and the like. With regard to the conventional microinjection device using a glass tube, the users have manually carried out the aspiration and elimination of a gene DNA solution by a hydraulic mechanism or the positioning of the needlepoint to the cell, and thus a certain level of skill has been required. However, with the structure of the present invention, the cell nucleus 27 is recognized using the image processing of the cell, and the needlepoint is positioned in the center of the cell nucleus 27. The subsequent operations are easily automated. Thus, the present invention requires no such level of skill.

In the aforementioned embodiment, a step of introducing different gene DNA into each cell is described. However, since the needle 21 is extremely thin, causing no substantial damage to the cell, multiple gene DNAs can also be introduced into a single cell.

Figure 8:
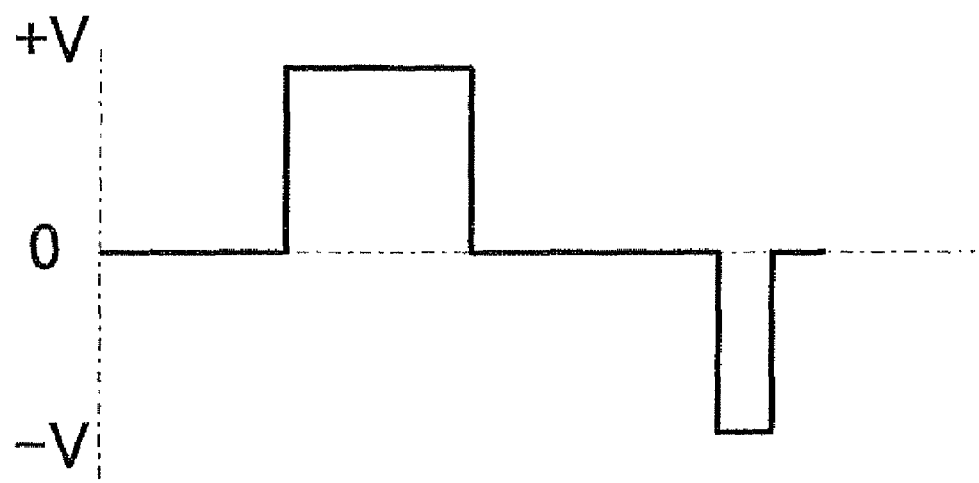
FIG. 8 shows an example of the voltage pattern of the applied voltage.
Figure 9:
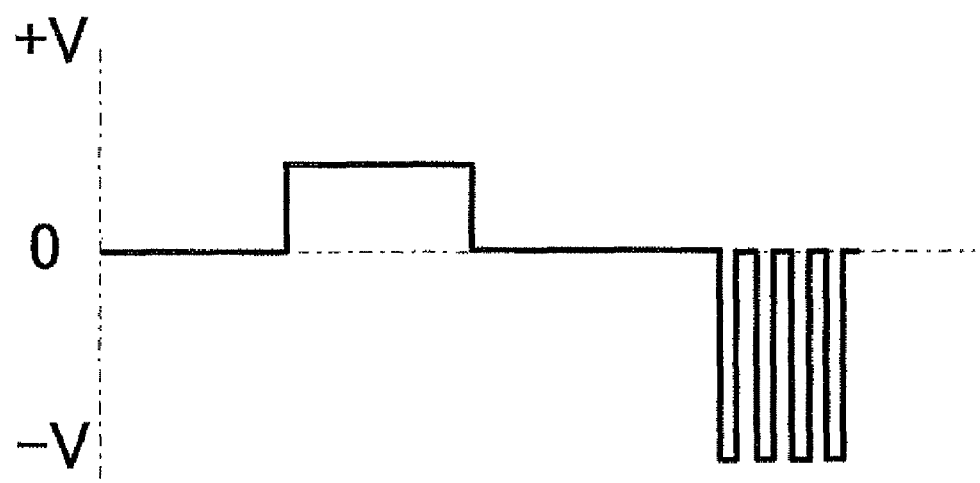
FIG. 9 shows another example of the voltage pattern of the applied voltage.

In addition, the voltage to be applied to the needlepoint is not limited to the aforementioned example. The voltage patterns shown in FIGS. 8 and 9 may also be applied, for example. In FIG. 8, the time required for retaining gene DNA is reduced, and the amount of such gene DNA attached to the needlepoint can thereby be reduced. That is, the amount of gene DNA to be introduced depends on the amount of gene DNA attached to the needlepoint. Thus, if the voltage value is decreased and the time required for application of the voltage is reduced, the amount of gene DNA attached is reduced. On the contrary, if the opposite operation is carried out, the amount attached can be increased, and the amount introduced can thereby also be increased. These operations are effective as means for changing the level of gene introduction to cells (making difference in the level of gene introduction to cells). In addition, in FIG. 9, when gene DNA is released into the cell nucleus, pulse voltages are applied to the needlepoints at short intervals (voltages that change over time), so that the action of removing gene DNA attached to the needle therefrom can be promoted, and so that almost all amount of gene DNA can be removed. It cannot be said that application of voltages has no influence upon the cell, and it may become stimulation. Accordingly, the shorter the time required for application of voltages, more preferable it is. For example, a voltage to be applied is set to be −1 V, and 10 pulses of such voltages are applied at 10 Hz.

The stacked piezoelectric actuator 22 used for the fine movement of the needle can be displaced at a high speed, substantially depending on application of a voltage. For example, the natural frequency of a stacked piezoelectric actuator 22 having a cross section of 5 mm square and a length of 20 mm in the bending direction is several kHz. The needlepoint moves in response to the voltage pattern at less than the above frequency (less than the resonant region). Thus, the needle 21 is inserted into the cell 26 at a high speed of several Hz, and the needle 21 is then lifted upwards at that cycle. By applying the aforementioned multiple pulse voltages during the short time from insertion to removal, the time required for the needle 21 to stay in the cell 26 can also be reduced, thereby reducing the invasiveness of the needle to the cell 26.

Figure 10:
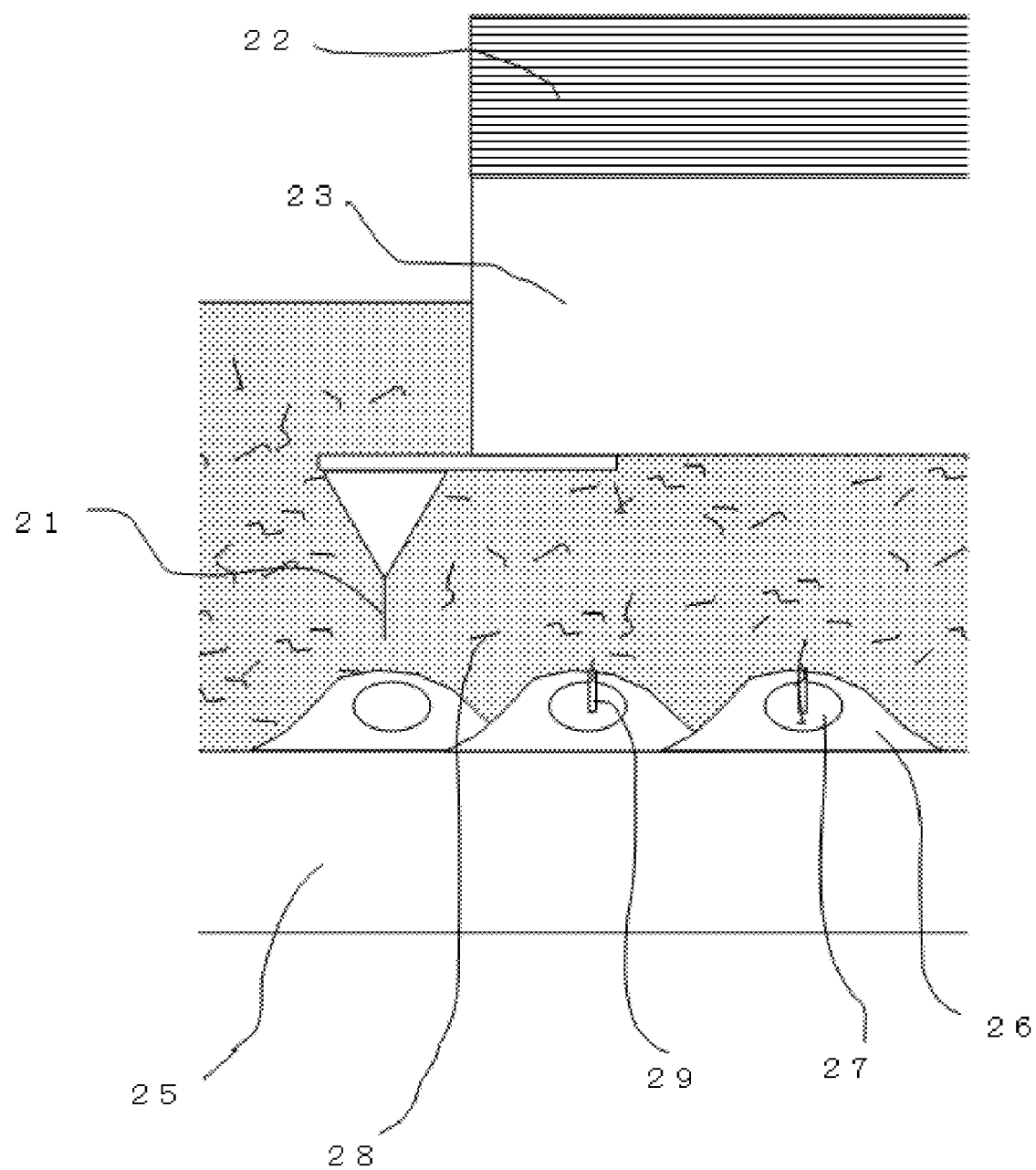
FIG. 10 shows a schematic view showing a case where gene DNA to be introduced into a cell is dispersed in a culture solution.

A case where gene DNA to be introduced into a cell is dispersed in a culture solution, as shown in FIG. 10, will be described below. The needle 21 used for gene introduction is moved up and down at a higher speed (1 cycle frequency consisting of several kHz) by the stacked piezoelectric actuator 22, so as to form a pinhole 29 on the cell membrane (cell nucleus 27). As described above, since the needle 21 has a very small diameter, insertion of such a needle has only little influence upon the cell 26. Moreover, by inserting and removing the needle 21 at a high speed, damage to the cell 26 can be further reduced. Thereby, a pathway for introducing gene DNA contained in a solution into the cell 26 (into the cell nucleus 27) is secured. By performing culture in such a state, the gene DNA in the solution can be introduced into the cell. Accordingly, by forming one or more pinholes in each of the cells 26 by automatic movement, gene DNA can easily and simply be introduced into multiple cells.

Preferably, a positive voltage is applied to the needle in a culture solution, in which gene DNA 28 is dispersed, and the gene DNA is retained on the surface of the needle. Multiple negative pulse voltages are applied during the time at which the needle is inserted into the cell, so as to release the gene DNA into the cell. The needle moves in the XY face in the culture solution, so that the gene DNA can successively be introduced into different cells. The operation to immerse the needle in a vessel so as to retain gene DNA on the surface of the needle, the washing operation, and the like, can be omitted, and thereby such gene DNA can be introduced into a large number of cells. Thus, the introduction efficiency is also increased.

Thereafter, the cell, into which a gene has been introduced as mentioned above, is continuously cultured in an incubator equipped in a microscope, thereby enabling observing and/or measuring over time, the process up to the expression of the gene, or the interaction between cells.

The present invention will be more specifically described in the following examples. However, the examples are not intended to limit the scope of the present invention.

EXAMPLES

Example 1

Using the device shown in FIG. 1, DNA was introduced into nerve cells that were cultured in a petri dish for culture.

As nerve cells, PC12 cells (nervous system clone cells isolated from rat adrenal medulla pheochromocytoma) were used. As a medium, DMEM (Dulbecco's Modified Eagle Medium) containing 10% fetal bovine serum (FBS) was used. The culturing was carried out at 37° C. in 5% $CO_2$. As DNA, a recombinant expression vector containing NGF receptor gene was used, and 1 μg/ml DNA solution was used.

Figure 11:
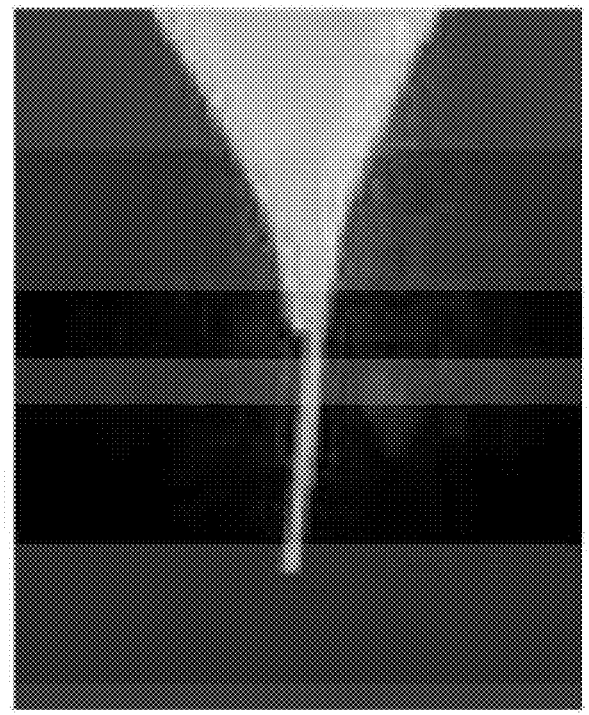
FIG. 11 shows a needle composed of a carbon nanotube, which has a diameter of 50 nm and a length of 3 μm.

The needle used for the device shown in FIG. 1 composed of the carbon nanotube shown in FIG. 11, which had a diameter of so nm and a length of 3 μm.

First, the needle was immersed in the DNA solution, so as to allow DNA to attach to the surface thereof. Thereafter, the needle was inserted into the nucleus of a nerve cell, and then released the DNA therein. After completion of the introduction of the DNA, the nerve cell was continuously cultured. Even 3 days later, the nerve cell still survived.

Figure 12:
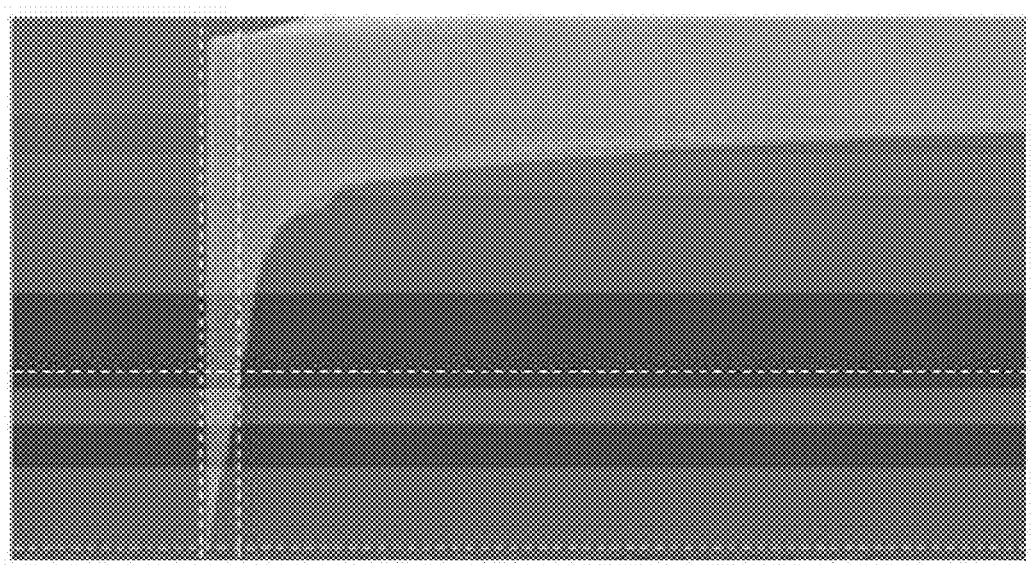
FIG. 12 shows a needle produced by narrowing the diameter of a cantilever made from silicon by etching, and forming a platinum layer on the surface thereof.

In the case of the needle shown in FIG. 12, the cantilever thereof made from silicon was etched for acumination, and a platinum layer was formed on the surface thereof. Using this needle, DNA was introduced into Hela cells. As a result, it was found that even 3 days after DNA introduction, the Hela cells still survived.

On the other hand, as a control, microinjection was carried out using a glass pipette (inside diameter: 300 μm) filled with the same above DNA solution, instead of using the needle composed of a carbon nanotube with a diameter of 50 nm and a length of 3 μm. After completion of the microinjection, the nerve cells were continuously cultured. However, the nerve cells died until 3 days later, and no surviving cells existed.

INDUSTRIAL APPLICABILITY

The present invention provides a method for introducing a physiologically active substance such as any given gene into any given cell that is in a view under a microscope, while significantly reducing invasiveness to the cell, and a device used for the above method.

The invention claimed is:

1. A microinjection method for introducing a physiologically active substance comprising deoxyribonucleic acid (DNA), ribonucleic acid (RNA) or a protein into a cell in a culture solution, which comprises: allowing the physiologically active substance to be diffused in the culture solution, and controlling movement of a needle, which is inserted into the cell, with respect to the cell in the culture solution where the physiologically active substance is diffused, securing a pathway for introducing the physiologically active substance in the culture solution in the cell by the movement of the needle.

* * * * *